US008828363B2

(12) United States Patent
Eirew

(10) Patent No.: US 8,828,363 B2
(45) Date of Patent: Sep. 9, 2014

(54) PHARMACEUTICAL COMPOSITION FOR IMPROVING ORAL HYGIENE AND METHODS THEREOF

(76) Inventor: Gary H. Eirew, Moreno Valley, CA (US)

( * ) Notice: Subject to any disclaimer, the term of this patent is extended or adjusted under 35 U.S.C. 154(b) by 2044 days.

(21) Appl. No.: 11/833,530

(22) Filed: Aug. 3, 2007

(65) Prior Publication Data

US 2009/0035229 A1    Feb. 5, 2009

(51) Int. Cl.
*A61Q 11/00*    (2006.01)
(52) U.S. Cl.
USPC .............................. 424/52; 424/49
(58) Field of Classification Search
CPC ...................................... A61Q 11/00
USPC ..................................... 424/49, 52
See application file for complete search history.

(56) References Cited

U.S. PATENT DOCUMENTS

| | | | |
|---|---|---|---|
| 6,309,625 B1 * | 10/2001 | Jensen et al. | 424/49 |
| 2003/0211052 A1 * | 11/2003 | Georgiades | 424/49 |
| 2006/0099156 A1 * | 5/2006 | MacDonald et al. | 424/53 |

* cited by examiner

*Primary Examiner* — Jeffrey S. Lundgren
*Assistant Examiner* — Chris Simmons
(74) *Attorney, Agent, or Firm* — Ladas & Parry LLP

(57) ABSTRACT

An aqueous based pharmaceutical composition for use as a oral hygienic treatment is described. The composition contains a pharmaceutically effective amount of a tetracycline-based antibiotic; a water-soluble calcium salt that aids in solubilizing the tetracycline-based antibiotic; a thickener; a pH adjustment agent; an antifoaming agent; an excipient; a surfactant; a preservative; and a flavoring agent. A method of making the aqueous based pharmaceutical composition includes the steps of adjusting, defoaming, dispensing, dispersing, dissolving, flavoring, heating, minimizing, pouring, solubilizing, suspending, and sweetening. A method of using the aqueous based pharmaceutical composition is also disclosed which includes the steps of expectorating, gargling, obtaining, pouring, receiving, and swishing.

6 Claims, No Drawings

PHARMACEUTICAL COMPOSITION FOR IMPROVING ORAL HYGIENE AND METHODS THEREOF

FIELD OF THE INVENTION

The present invention relates to dental hygiene acessories, more particularly to an aqueous based pharmaceutical composition for use in inhibiting and controlling populations of microorganisms in the oral cavity.

DESCRIPTION OF THE PRIOR ART

Oral cavity diseases may include periodontitis, gingivitis, dental caries, halitosis, and plaque formation. Poor oral hygiene has been implicated as a primary causative factor in many oral diseases and the resultant bacterial infestations are well known disease agents in these oral cavity diseases. For example, periodontal diseases, which include periodontitis and gingivitis, are thought to be caused by poor dental hygiene and subsequently exploited by bacteria, such as *Porphyromonas gingivalis*, that form plaques on the surfaces of the teeth at the gingival sulcus or pocket.

Treatment methods depend upon the severity of the disease. Prevention treatment methods range from using simple mouthwashes to brushing teeth. Disease treatment methods range from filing dental caries (tooth decay) to tooth extraction via dental surgery. In almost all cases, treatment regimens involving medicated dentifrices and/or oral rinses are recommended to maintain a healthy oral environment as effective preventative therapies. Mild oral diseases, such as tartar buildup (simple calculus), are generally treated by the mechanical removal of the irritants. Interproximal (i.e., between teeth) cleaning is also important in maintaining a healthy oral cavity free of gingival sulcus. Unfortunately even mild cases of periodontal diseases through time may progress in becoming more severe, and as a consequence even pedantic cleaning with common dentifrices can only prolong the progression of these diseases.

Mouthwash and oral rinses are well known in the dental arts and are liquid preparations that are specifically designed to cleanse and refresh the mouth. People for many years have been using theses rinses to prevent bad breath and to control oral microorganism populations that cause tooth decay, plaque and gum diseases. Active agents added into mouthwashes have usually been confined to ethanol (i.e., alcohol) that acts as a disinfectant and preservative but ethanol based mouth rinses may result in undesirable side effects, such as chemical burning of the inner lining of the oral cavity. Obviously, there is a need to develop more effective dental health care products for use in maintaining a healthy oral environment.

A large number of oral hygiene products are presently available on the market. However, over the counter mechanical measures alone do not appear to be entirely successful in maintaining periodontal health. In particular, gingivitis is a particularly difficult disease to control. Therefore, dental research has been focused on making available alternate means for maintaining and controlling oral hygiene.

SUMMARY OF THE INVENTION

The present pharmaceutical composition and associated methods, according to the principles of the present invention, overcomes a number of the shortcomings of the prior art by providing a novel aqueous based pharmaceutical composition and associated methods for use in improving the oral hygiene. The aqueous based pharmaceutical composition includes a pharmaceutically effective amount of a tetracycline-based antibiotic; a water-soluble calcium salt that aids in solubilizing the tetracycline-based antibiotic; a thickener; a pH adjustment agent; an antifoaming agent; an excipient; a surfactant; a preservative; and a flavoring agent. The method of making the aqueous based pharmaceutical composition includes the steps of adjusting, defoaming, dispensing, dispersing, dissolving, flavoring, heating, minimizing, pouring, solubilizing, suspending, and sweetening. A method of using the aqueous based pharmaceutical composition is also disclosed which includes the steps of expectorating, gargling, obtaining, pouring, receiving, and swishing.

In view of the foregoing disadvantages inherent in the known type aqueous based pharmaceutical compositions now present in the prior art, the present invention provides an improved aqueous based pharmaceutical composition, which will be described subsequently in great detail, is to provide a new and improved aqueous based pharmaceutical composition which is not anticipated, rendered obvious, suggested, or even implied by the prior art, either alone or in any combination thereof.

To attain this, the present invention essentially comprises a tetracycline-based antibiotic; a water-soluble calcium salt that aids in solubilizing the tetracycline-based antibiotic; a thickener; a pH adjustment agent; an antifoaming agent; an excipient; a surfactant; a preservative; and a flavoring agent.

There has thus been outlined, rather broadly, the more important features of the invention in order that the detailed description thereof that follows may be better understood, and in order that the present contribution of the art may be better appreciated.

The invention may also include an optional flavoring agent, coloring agent, and a fluoride source.

Numerous objects, features and advantages of the present invention will be readily apparent to those of ordinary skill in the art upon reading of the following detailed description of presently preferred, but nonetheless illustrative, embodiments of the present invention when taken in conjunction with the accompany drawings. In this respect, before explaining the current embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

By the phrase "pharmaceutically effective amount" of an agent as provided herein is meant a nontoxic but sufficient amount of the agent to provide the desired effect.

As used herein, the phrase "also known as" is not intended to be limiting and is used in the same way that the term "comprising" is commonly used.

As such, those skilled in the art will appreciate that the conception, upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an aspect of the present invention to provide a new and improved aqueous based pharmaceutical composition that has many of the advantages of the prior aqueous based pharmaceutical composition and minimizing a number of their disadvantages.

It is another aspect of the present invention to provide a new and improved aqueous based pharmaceutical composition that may be easily and efficiently manufactured and marketed.

An even further aspect of the present invention is to provide a new and improved aqueous based pharmaceutical composition that has a low cost of manufacture with regard to both materials and labor, and which accordingly is then susceptible of low prices of sale to the consuming public, thereby making an aqueous based pharmaceutical composition economically available to the buying public.

Still another aspect of the present invention is to provide an aqueous based pharmaceutical composition that provides in the apparatuses and methods of the prior art some of the advantages thereof, while simultaneously overcoming some of the disadvantages normally associated therewith.

Even still another aspect of the present invention is to provide an aqueous based pharmaceutical composition having a pharmaceutically effective amount of a tetracycline-based antibiotic such as doxycycline for use in inhibiting and controlling populations of microorganisms in the oral cavity.

Still another aspect of the present invention is to provide a method of making the aqueous based pharmaceutical composition comprising the steps of adjusting, defoaming, dispensing, dispersing, dissolving, flavoring, heating, minimizing, pouring, solubilizing, suspending, and sweetening.

Still yet another aspect of the present invention is to provide a method of using the aqueous based pharmaceutical composition is also disclosed which includes the steps of expectorating, gargling, obtaining, pouring, receiving, and swishing.

Further, the purpose of the foregoing abstract is to enable the U.S. Patent and Trademark Office and the public generally, and especially the scientist, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

These together with other objects of the invention, along with the various features of novelty that characterize the invention, are pointed out with particularity in the claims annexed to and forming a part of this disclosure. For a better understanding of the invention, its operating advantages and the specific objects attained by its uses, reference should be had to the accompanying drawings and description matter in which there are illustrated preferred embodiments of the invention.

DETAILED DESCRIPTION OF THE PREFERRED EMBODIMENT

One preferred embodiment of an aqueous based pharmaceutical composition for use as a oral hygienic treatment comprises: a pharmaceutically effective amount of a tetracycline-based antibiotic; a water-soluble calcium salt; a thickener; a pH adjustment agent; an antifoaming agent; an excipient; a surfactant; a preservative; and a flavoring agent.

A more preferred embodiment of the composition includes the tetracycline-based antibiotic comprises doxycycline; the water-soluble calcium salt comprises calcium chloride; the thickener comprises sodium carboxymethylcellulose; the pH adjustment agent establishing a pH of the composition between about 5 to 9; the antifoaming agent comprises simethicone; the excipient comprises glycerin; the surfactant comprises polysorbate 20; the preservative comprises sodium metabisulfite, methylparabene, and propylparaben; and the flavoring agent is selected from the group consisting of artificial banana creme, lemon oil, and tangerine oil.

Another preferred embodiment of the composition includes the tetracycline-based antibiotic comprises doxycycline at a concentration between about 10 to 20 mg/ml; the water-soluble calcium salt comprises calcium chloride at a concentration of about 1 to 3 mg/ml; the thickener comprises sodium carboxymethylcellulose at a concentration of about 3 to about 20 mg/ml; the pH adjustment agent establishing the pH of the composition between about 6 to 8; the antifoaming agent comprises simethicone at a concentration between about 1 to 10 mg/ml; the excipient comprises glycerin at a concentration between about 50 to about 300 mg/ml; the surfactant comprises polysorbate 20 at a concentration about 0.1 to about 5 mg/ml; the preservative comprises sodium metabisulfite at a concentration between about 0.1 to about 5 mg/ml, methylparabene at a concentration between about 0.1 to about 7 mg/ml, and propylparaben at a concentration between about 0.1 to about 3 mg/ml; and the flavoring agent is selected from the group consisting of artificial banana creme at a concentration between about 10 to 60 mg/ml, lemon oil at a concentration between about 1 to 5 mg/ml, and tangerine oil at a concentration between about 10 to 50 mg/ml.

Yet another preferred embodiment of the composition includes: the tetracycline-based antibiotic comprises doxycycline at a concentration about 15 mg/ml; the water-soluble calcium salt comprises calcium chloride at a concentration about 1.7 mg/ml; the thickener comprises sodium carboxymethylcellulose at a concentration of about 8.3 mg/ml; the pH adjustment agent establishing the pH of the composition between about 7.0 to 7.5; the antifoaming agent comprises simethicone at a concentration between about 4.2 mg/ml; the excipient comprises glycerin at a concentration between about 167 to about mg/ml; the surfactant comprises polysorbate 20 at a concentration about 0.125 mg/ml; the preservative comprises sodium metabisulfite at a concentration between about 1.0 mg/ml, methylparabene at a concentration between about 1.3 mg/ml, and propylparaben at a concentration about 0.25 mg/ml; and the flavoring agent is selected from the group consisting of artificial banana creme at a concentration about 30 mg/ml, lemon oil at a concentration about 2.5 mg/ml, and tangerine oil at a concentration about 27 mg/ml.

The aqueous based pharmaceutical composition may be formed into any known form as long as it is suitable for oral administration. Accordingly, the aqueous based pharmaceutical composition may take a form for a tooth paste, a tooth powder, a dental floss, a liquid dentrifice, a mouthwash, a mouth rinse, a chewing gum, a gargle, a troche, a cream, an ointment, a gel, a spray, a lozenge, and even a hard-candy.

The tetracycline-based antibiotic may be any commercially available tetracycline-based antibiotic derivative. Some preferred embodiments of the tetracycline-based antibiotic may be selected from the group consisting of tetracycline, chlortetracycline, oxytetracycline, demeclocycline, doxycycline, lymecycline, meclocycline, methyacycline, minocycline, rolitetracycline, and mixtures thereof. The tetracycline antibiotic is also known as 2-(amino-hydroxy-methylidene)-4-dimethylamino-6,10,11,12a-tetrahydroxy-6-methyl-4,4a,5,5a-tetrahydrotetracene-1,3,12-trione which has a CAS (Chemical Abstract Service) registration number of 60-54-8. The chlortetracycline is also known as of (Z,4S, 4aS,5aS,6S5,12aS)-2-(amino-hydroxy-methylidene)-7-chloro-4-dimethylamino-6,10,11,12a-tetrahydroxy-6-methyl-4,4a,5,5a-tetrahydrotetracene-1,3,12-trione which has a CAS registration number of 57-62-5. The oxytetracycline is also known as (2Z,4S,4aS,5aS,6S,12aS)-2-(amino-hydroxy-methylidene)-7-chloro-4-dimethylamino-6,10,11,12a-tetrahydroxy-6-methyl-4,4a,5,5a-tetrahydrotetracene-1,3,12-trione which has a CAS registration number of 79-57-2. The demeclocycline is also known under the IUPAC nomenclature as (2Z,4S,4aS,5aS,6S,12aS)-2-(amino-hydroxy-methylidene)-7-chloro-4-dimethylamino-6,10,11,12a-tetrahydroxy-6-methyl-4,4a,5,5a-tetrahydrotetracene-1,3,12-trione which has a CAS registration number of 127-33-3. The doxycycline is also known as (2-(amino-hydroxy-methylidene)-4-dimethylamino-5,10,11,12a-tetrahydroxy-6-methyl-4a,5,5a,6-tetrahydro-4H-tetracene 1,3,12-trione which has a CAS registration number of 564-25-0. The lymecycline is also known as 2-(amino-hydroxy-methylidene)-7-chloro-4dimethylamino-6,10,11,12a-tetrahydroxy-6-methyl-4,4a,5,5a-tetrahydrotetracene-1,3,12-trione which has a CAS registration number of 992-21-2. The minocycline is also known as 2-(amino-hydroxy-methylidene)-4,7-bis(dimethylamino)-10,11,12a-trihydroxy-4a,5,5a,6-tetrahydro-4H-tetracene-1,3,12-trione which has a CAS registration number of 10118-90-8.

The water-soluble calcium salt may be any calcium salt as long as it is water soluble and generally known to be safe and non-toxic when exposed the oral cavity of humans. Some preferred embodiments of the water-soluble calcium salt may be selected from the group consisting of calcium acetate, calcium benzoate, calcium bromide, calcium butyrate, calcium carbonate, calcium chloride, calcium citrate, calcium formate, calcium fumarate, calcium fluoride, calcium hydroxide, calcium gluconate, calcium glycerophosphate, calcium isobutyrate, calcium lactate, calcium malate, calcium maleate, calcium nitrate, calcium phosphate, calcium propionate, and mixtures thereof.

The thickener may be any commercially available thickener as long as it is generally known to be generally known as safe and non-toxic when exposed the oral cavity of humans. Some preferred embodiments of the thickener may be selected from the group consisting of alginates, alginic acid, arabic gums, carbomer, carboxyethylene, cellulose derivatives, carboxymethylcellulose, chitosan, carboxypolymethylene, crystalline cellulose, carob bean gum, carrageenan, curdlan, chitin, chitosan, chitosamine, carboxymethyl cellulose, carboxymethylcellulose sodium, carboxy methylcellulose calcium, ethylcellulose, ethylhydrooxyethylcellulose, hydroxypropylmethylcellulose, hydroxypropylcellulose, hydroxyethylcellulose, natural gums, gellan gum, guar gum, hydroxyethylcellulose, hydroxypropylcellulose, hydroxyethylmethylcellulose, hydroxypropylmethylcellulose, karaya gum, lactose, methylcellulose, polyvinyl pyrrolidone, polyoxyethylenated polyoxypropylene polyol, polyacrylic acid, polyvinylpyrrolidone derivatives, polyoxyethylene polyoxypropylene copolymers, polyvinyl alcohol, pectin, propylene glycol alginate ester, starch sodium glycolate, starch phosphate ester sodium, sodium polyacrylate, sodium alginate, Tara gum, tamarind seed gum, tragacanth gum, veegum, xanthan gum, and mixtures thereof.

The pH adjustment agent may be any known commercially available pH adjustment agent as long as it is generally known to be safe and non-toxic during exposure to humans in the oral cavity. Some preferred embodiments of pH adjustment agents may be selected from the group consisting of acetate buffers, aminomethylamine buffers, ammonium hydroxide, benzoate buffers, borate buffers, carbonate buffers, citrate buffers, diethylamine buffers, diisopropylamine buffers, hydrochloric acid, lactic acid buffers, perchloric acid, aphosphate buffers, tartric acid, triethylamine buffers, proprioate buffers, sodium hydroxide, tetrahydroxypropylethylendiamine buffers, and mixtures thereof.

The antifoaming agent may be any commercially available antifoaming agent as long as it is generally known to be safe and non-toxic during exposure to humans in the oral cavity. Some preferred embodiments of the antifoaming agent may be selected from the group consisting of dimethicone, simethicone, and mixtures thereof.

The excipient may be any commercially available excipient as long as it is generally known to be safe and non-toxic during exposure to humans in the oral cavity. Some preferred embodiments of the excipient may be selected from the group consisting of 1,3-butylene glycol, ethylene glycol, glycerin, lactit, multit, propylene glycol, polyethylene glycol, polypropylene glycol, sorbitol, xylitol, ethanol, and mixtures thereof.

The surfactant may be any commercially available surfactant as long as it is generally known to be safe and non-toxic during exposure to humans in the oral cavity. Some preferred embodiments of the surfactant may be selected from the group consisting of PEG-10 laurate, PEG-12 laurate, PEG-20 laurate, PEG-32 laurate, PEG-32 dilaurate, PEG-12 oleate, PEG-15 oleate, PEG-20 oleate, PEG-20 dioleate, PEG-32 oleate, PEG-200 oleate, PEG-400 oleate, PEG-15 stearate, PEG-32 distearate, PEG-40 stearate, PEG-100 stearate, PEG-20 dilaurate, PEG-25 glyceryl trioleate, PEG-32 dioleate, PEG-20 glyceryl laurate, PEG-30 glyceryl laurate, PEG-20 glyceryl stearate, PEG-20 glyceryl oleate, PEG-30 glyceryl oleate, PEG-30 glyceryl laurate, PEG-40 glyceryl laurate, PEG-40 palm kernel oil, PEG-50 hydrogenated castor oil, PEG-40 castor oil, PEG-35 castor oil, PEG-60 castor oil, PEG-40 hydrogenated castor oil, PEG-60 hydrogenated castor oil, PEG-60 corn oil, PEG-6 caprate/caprylate glycerides, PEG-8 caprate/caprylate glycerides, polyglyceryl-10 laurate, PEG-30 cholesterol, PEG-25 phyto sterol, PEG-30 soya sterol, PEG-20 trioleate, PEG-40 sorbitan oleate, PEG-80 sorbitan laurate, polysorbate 20, polysorbate 80, POE-9 lauryl ether, POE-23 lauryl ether, POE-10 oleyl ether, POE-20 oleyl ether, POE-20 stearyl ether, tocopheryl PEG-100 succinate, PEG-24 cholesterol, polyglyceryl-10 oleate, Tween 40, Tween 60, sucrose monostearate, sucrose monolaurate, sucrose monopalmitate, PEG 10-100 nonyl phenol series, PEG 15-100 octyl phenol series, a poloxamer, sodium lauroyl sarcosinate, sodium alkyl sulfate, cocoamidopropyl betaine, and mixtures thereof.

The preservative may be any commercially available preservative as long as it is generally known to be safe and non-toxic during exposure to humans in the oral cavity. Some preferred embodiments of the preservative is selected from the group consisting of ascorbic acid, ascorbyl palmitate, benzyl alcohol, bisulfite salts, butylated hydroxyanisole, butylhydroxytoluene, butylparaben, chloromethylisotiazolinone, chlorophenesin, cysteine, citric add, diazolidinyl urea, ethylenediamine tetraacetic salts, ethylparaben, hydroxide salts, imidazolidinyl urea, isobutylparaben, metabisulfite salts, methychloroisothiazolinone, methylisothiazolinone, methyl para ben, propylparaben, phenoxyethanol, phytic acid, propyl gallate, sodium benzoate, sorbic acid, thiosulfate salts, d-α-tocopherol, d-β-tocopherol, d-γ-tocopherol, and d-δ-tocopherol ) and d-α-tocotrienol, d-β-tocotrienol, d-γ-tocotrienol, d-δ-tocotrienol, triethanolamine, thioglycerol, and mixtures thereof.

An optional flavoring agent may be added to the composition as long as long as it is generally known to be safe and non-toxic during exposure to humans in the oral cavity. Some preferred embodiments of the flavoring agent may be selected from the group consisting anise, artificial banana creme, cassia, citric oil, lemon oil, lime oil, lemongrass oil, orange oil, sweet orange oil, grapefruit oil, pomegranate oil, apricot oil extract, tangerine extract, tangelo oil, peppermint oil, spearmint oil, sage oil, rosemary oil, cinnamon oil, winter green oil, clove oil, eucalyptus oil, ginger oil, sassafras oil, menthol, arvensis mint oil, synthetic mint flavors and oils, carvone, methyleugenol, methyl salicylate, methyl eugenol, thymol, anethole, millefolium extract, chamomile, lavender oil, myrrh, eugenol, tea tree oil, sage oil, mallow, limonene, ocimene, n-decyl alcohol, citronellol, α-terpineol, linalol, ethyllinalol, thyme, almond oil, nutmeg, vanillin, and mixtures thereof.

An optional fluoride ion source may be added to the composition as long as it is generally known to be safe and non-toxic during exposure to humans in the oral cavity. Some preferred embodiments of the optional fluoride ion source may be selected from the group consisting of sodium fluoride, potassium fluoride, ammonium fluoride, calcium fluoride, cuprous fluoride, zinc fluoride, barium fluoride, sodium flourosilicate, ammonium flourosilicate, sodium fluorozirconate, ammonium fluorozirconate, sodium monofluorophosphate, aluminum mono-and di-fluorophosphate, and fluorinated sodium calcium pyrophosphate, stannous fluorides, potassium stannous fluoride, sodium hexafluorostannate, stannous chlorafluoride, sodium fluorozirconate, sodium monofluorophosphate, and mixtures thereof An optional sweetening agent may be added to the composition as long as it is generally known to be safe and non-toxic during exposure to humans in the oral cavity. Some preferred embodiments of the optional sweetening agent may be selected from the group consisting of acefulfame-K, aspartane, asparatylpheylalanine methyl ester, cyclamate salts, fructose, glycyrrhizin, lactose, neohesperidyidihydrochalocone, perillartine,p-methoxycinnamic aldehyde, saccharin, stevioside, sodium cycliamate, sucrose, xylitol, sorbitoal mannitol, hydrogenated starch hydrolysates, maltitol, isomalt, erythritol, thaumatin, dihydrochalcones, acesulfame K compounds, sucralose, neotame, alitame, glycyrrhizin, stevioside, and mixtures thereof An optional coloring agent may be added to the composition as long as it is generally known to be safe and non-toxic during exposure to humans in the oral cavity. Some preferred embodiments of the optional coloring agent may be selected from the group consisting of FD & C Red No. 3, FD & C Yellow No. 5, FD & C Yellow No. 6, FD & C Green No. 3, FD & C Blue No. 1, and FD & C Blue No. 2, FD&C green No., and mixtures thereof.

One preferred embodiment of a method of making the aqueous based pharmaceutical composition for use as a oral hygienic treatment, the method comprising the steps of adjusting, defoaming, dispensing, dispersing, dissolving, flavoring, heating, minimizing, pouring, solubilizing, suspending, and sweetening. The heating step comprises heating purified water to make an aqueous preservative mixture comprising methyl paraben and propylparaben. The suspending step comprises suspending a thicken comprising sodium carboxymethylcellulose into the aqueous preservative mixture to make a gel. The dissolving step comprises dissolving another preservative comprising sodium metabisulfite into the gel to make a resulting gel. The dispersing step comprises dispersing a pharmaceutically effective amount of a tetracycline-based antibiotic comprising doxycycline into the resulting gel to make an activated gel. The solubilizing step comprises solubilizing a water-soluble calcium salt compromising calcium chloride to the activated gel to make a solubilized doxycycline gel to between about 7.0 to about 7.5 pH units to make a neutralized gel. The defoaming step comprises defoaming the neutralized gel with an antifoaming agent comprising simethicone and a surfactant comprising polysorbate into the neutralized gel to make a defoamed gel. The dispensing step comprises dispensing an excipient comprising glycerin into the defoamed gel to make an excipient gel. The sweetening step comprises sweetening the excipient gel with a sweetening agent comprising sorbitol to make a sweetened gel. The flavoring step comprises flavoring the sweetened gel with a flavoring agent selected from the group consisting of artificial banana crème, lemon oil, and tangerine oil to make a flavored concentrate. The pouring step comprises pouring purified water into the sweetened gel to a final volume to make the aqueous based pharmaceutical composition for use as a oral hygienic treatment. The minimizing step comprises minimizing exposure of the aqueous based pharmaceutical composition to ultraviolet lights.

One preferred method of using the aqueous based pharmaceutical composition for maintaining a healthy oral environment comprises the steps of expectorating, gargling, obtaining, pouring, receiving, and swishing. The obtaining step comprises obtaining an aqueous based pharmaceutical composition comprising: a pharmaceutically effective amount of a tetracycline-based antibiotic; a water-soluble calcium salt; a thickener; a pH adjustment agent; an antifoaming agent; an excipient; a surfactant; a preservative; and a flavoring agent. The pouring step comprises pouring an aliquot of the composition into a cup. The receiving step comprises receiving the aliquot of the composition into a mouth. The gargling step comprises gargling with the aliquot of the composition in the mouth. The swishing step comprises swishing the aliquot of the composition in the mouth to maximize exposure to the aliquot of the composition to the mouth. The expectorating step comprises expectorating out the swished aliquot from the mouth into a sink.

As to the manner of usage and operation of the present invention, the same should be apparent from the above description. Accordingly, no further discussion relating to the manner of usage and operation will be provided.

While a preferred embodiment of the aqueous based pharmaceutical composition and associated methods of using and making have been described in detail, it should be apparent that modifications and variations thereto are possible, all of which fall within the true spirit and scope of the invention. With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Throughout this specification, unless the context requires otherwise, the word "comprise" or variations such as "comprises or comprising" or the term "includes" or variations, thereof, or the term "having" or variations, thereof will be understood to imply the inclusion of a stated element or integer or group of elements or integers but not the exclusion of any other element or integer or group of elements or integers. In this regard, in construing the claim scope, an embodiment where one or more features is added to any of the claims is to be regarded as within the scope of the invention given that the essential features of the invention as claimed are included in such an embodiment.

Those skilled in the art will appreciate that the invention described herein is susceptible to variations and modifications other than those specifically described. It is to be understood that the invention includes all such variations and modification which fall within its spirit and scope. The invention also includes all of the steps, features, compositions and compounds referred to or indicated in this specification, individually or collectively, and any and all combinations of any two or more of said steps or features.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

I claim:

1. An aqueous based pharmaceutical composition for use as a oral hygienic treatment, the composition comprising:
 a pharmaceutically effective amount of a tetracycline-based antibiotic comprising doxycycline;
 a water-soluble calcium salt comprising calcium chloride;
 a thickener comprising carboxymethylcellulose;
 a pH adjustment agent which establishes a pH of the composition between about 5 to 9;
 an antifoaming agent comprising simethicone;
 an excipient comprising glycerine;
 a surfactant comprising polysorbate 20;
 a preservative comprising sodium metabisulfite, methylparaben and propylparaben; and
 a flavoring agent selected from the group consisting of artificial banana crème, lemon oil and tangerine oil.

2. The composition of claim 1 wherein
 the tetracycline-based antibiotic comprises doxycycline at a concentration between about 10 to 20 mg/ml;
 the water-soluble calcium salt comprises calcium chloride at a concentration of about 1 to 3 mg/ml;
 the thickener comprises sodium carboxymethylcellulose at a concentration of about 3 to about 20 mg/ml;
 the pH adjustment agent establishes the pH of the composition between about 6 to 8; the antifoaming agent comprises simethicone at a concentration between about 1 to 10 mg/ml;
 the excipient comprises glycerin at a concentration between about 50 to about 300 mg/ml;
 the surfactant comprises polysorbate 20 at a concentration about 0.1 to about 5 mg/ml;
 the preservative comprises sodium metabisulfite at a concentration between about 0.1 to about 5 mg/ml, methylparabene at a concentration between about 0.1 to about 7 mg/ml, and propylparaben at a concentration between about 0.1 to about 3 mg/ml; and
 the flavoring agent is selected from the group consisting of artificial banana creme at a concentration between about 10 to 60 mg/ml, lemon oil at a concentration between about 1 to 5 mg/ml, and tangerine oil at a concentration between about 10 to 50 mg/ml.

3. The composition of claim 1 wherein
 the tetracycline-based antibiotic comprises doxycycline at a concentration about 15 mg/ml;
 the water-soluble calcium salt comprises calcium chloride at a concentration about 1.7 mg/ml;
 the thickener comprises sodium carboxymethylcellulose at a concentration of about 8.3 mg/ml;
 the pH adjustment agent establishes the pH of the composition between about 7.0 to 7.5;
 the antifoaming agent comprises simethicone at a concentration at about 4.2 mg/ml;
 the excipient comprises glycerin at a concentration at about 167 mg/ml; the surfactant comprises polysorbate 20 at a concentration at about 0.125 mg/ml; the preservative comprises sodium metabisulfite at a concentration at about 1.0 mg/ml, methylparabene at a concentration at about 1.3 mg/ml, and propylparaben at a concentration about 0.25 mg/ml; and
 the flavoring agent is selected from the group consisting of artificial banana creme at a concentration about 30 mg/ml, lemon oil at a concentration about 2.5 mg/ml, and tangerine oil at a concentration about 27 mg/ml.

4. An aqueous based oral hygienic treatment pharmaceutical composition comprising a tetracycline-based antibiotic comprising
 doxycycline;
 calcium chloride;
 carboxymethylcellulose;
 a pH adjustment agent establishing a pH of between about 5 to 9;
 simethicone;
 glycerine;
 polysorbate 20;
 a preservative selected from the grouping consisting of sodium metabisulfite, methylparaben and propylparaben, and
 a flavoring agent selected from artificial banana crème, lemon oil or tangerine oil.

5. The composition of claim 4 wherein the tetracycline-based antibiotic comprises doxyclycine at a concentration between about 10 to 20 mg/ml;
 the tetracycline-based antibiotic comprises doxycycline at a concentration between about 10 to 20 mg/ml;
 calcium chloride at a concentration of about 1 to 3 mg/ml;
 carboxymethylcellulose at a concentration of about 3 to about 20 mg/ml;
 the pH adjustment agent establishing the pH of the composition between about 6 to 8; simethicone at a concentration between about 1 to 10 mg/ml;
 glycerin at a concentration between about 50 to about 300 mg/ml;
 polysorbate 20 at a concentration about 0.1 to about 5 mg/ml;
 the preservative selected from the group consisting of sodium metabisulfite at concentration between about 0.1 to about 5 mg/ml, methylparaben at concentration between about 0.1 to about 7 mg/ml, and propylparaben at a concentration between about 0.1 to about 3 mg/ml; and
 the flavoring agent is selected from the group consisting of artificial banana creme at a concentration between about 10 to 60 mg/ml, lemon oil at a concentration between about 1 to 5 mg/ml, and tangerine oil at a concentration between about 10 to 50 mg/ml.

6. The composition of claim 5 wherein
 the tetracycline-based antibiotic comprises doxycycline at a concentration at about 15 mg/ml;
 calcium chloride at a concentration of about 1.7 mg/ml;
 carboxymethylcellulose at a concentration of about 8.3 mg/ml;
 the pH adjustment agent establishes the pH of the composition between about 7 to 7.5; simethicone at a concentration at about 4.2 mg/ml;
 glycerin at a concentration at about 167 mg/ml;
 polysorbate 20 at a concentration at about 0.125 mg/ml;

the preservative comprises sodium metabisulfite at a concentration at about 1.0 mg/ml, methylparaben at a concentration about 1.3 mg/ml, propylparaben at a concentration about 0.25 mg/ml; and the flavoring agent is selected from the group consisting of artificial banana creme at a concentration about 30 mg/ml, lemon oil at a concentration about 2.5 mg/ml, and tangerine oil at a concentration about 27 mg/ml.

* * * * *